(12) United States Patent
Säll et al.

(10) Patent No.: US 11,213,625 B2
(45) Date of Patent: Jan. 4, 2022

(54) COMMUNICATION DEVICE FOR TRANSMITTING INFORMATION FROM A MEDICAMENT DELIVERY DEVICE

(71) Applicant: CAREBAY EUROPE LTD, Sliema (MT)

(72) Inventors: Daniel Säll, Segeltorp (SE); Daniel Carlsson, Enskede (SE)

(73) Assignee: SHL MEDICAL AG, Zug (CH)

( * ) Notice: Subject to any disclaimer, the term of this patent is extended or adjusted under 35 U.S.C. 154(b) by 756 days.

(21) Appl. No.: 16/061,050

(22) PCT Filed: Nov. 16, 2016

(86) PCT No.: PCT/EP2016/077805
§ 371 (c)(1),
(2) Date: Jun. 11, 2018

(87) PCT Pub. No.: WO2017/108277
PCT Pub. Date: Jun. 29, 2017

(65) Prior Publication Data
US 2018/0361067 A1 Dec. 20, 2018

(30) Foreign Application Priority Data
Dec. 22, 2015 (EP) ..................................... 15202193

(51) Int. Cl.
*A61M 5/20* (2006.01)
*A61M 5/28* (2006.01)
(Continued)

(52) U.S. Cl.
CPC ............ *A61M 5/2033* (2013.01); *A61M 5/28* (2013.01); *A61M 5/31568* (2013.01);
(Continued)

(58) Field of Classification Search
CPC .... A61M 5/1454; A61M 5/20; A61M 5/2033; A61M 5/24; A61M 5/28; A61M 5/31551;
(Continued)

(56) References Cited

U.S. PATENT DOCUMENTS

2002/0188419 A1  12/2002  Slate et al.
2010/0102799 A1   4/2010  Schnidrig
(Continued)

FOREIGN PATENT DOCUMENTS

CN  101405582 A  4/2009
CN  101721761 A  6/2010
(Continued)

OTHER PUBLICATIONS

International Search Report and Written Opinion for Int. App. No. PCT/EP2016/077805, dated Feb. 1, 2017.

*Primary Examiner* — Theodore J Stigell
*Assistant Examiner* — Larry R. Wilson
(74) *Attorney, Agent, or Firm* — McDonnell Boehnen Hulbert & Berghoff LLP

(57) ABSTRACT

A communication device for a medicament delivery device is presented that includes at least one translation detection arrangement, configured to detect a translation of at least one physical part of the medicament delivery device by utilization of a resilience and an electrical conductivity for at least one spring of the medicament delivery device. Also included is at least one change of state detection unit, configured to detect at least one change of state for the medicament delivery device based on the detected translation. The communication device further includes at least one activation unit, configured to activate the at least one change of state detection unit based on the at least one detected translation. The communication device also includes at least one transmission unit configured to provide a wireless transmission of
(Continued)

information related to the at least one change of state to an external receiving device.

20 Claims, 12 Drawing Sheets

(51) Int. Cl.
*A61M 5/315* (2006.01)
*A61M 5/32* (2006.01)

(52) U.S. Cl.
CPC ... *A61M 5/3257* (2013.01); *A61M 2205/3317* (2013.01); *A61M 2205/3561* (2013.01); *A61M 2205/50* (2013.01); *A61M 2205/581* (2013.01); *A61M 2205/582* (2013.01); *A61M 2205/583* (2013.01); *A61M 2205/587* (2013.01); *A61M 2205/6009* (2013.01); *A61M 2205/6018* (2013.01)

(58) Field of Classification Search
CPC .......... A61M 5/31555; A61M 5/31568; A61M 5/3157; A61M 5/31578; A61M 5/3158; A61M 5/31581; A61M 5/3243; A61M 5/3257; A61M 5/326; A61M 5/3267; A61M 2005/14506; A61M 2005/206; A61M 2005/208; A61M 2005/3142; A61M 2205/3317; A61M 2205/3553; A61M 2205/3561; A61M 2205/3576; A61M 2205/50; A61M 2205/52; A61M 2205/581; A61M 2205/582; A61M 2205/583; A61M 2205/587; A61M 2205/6009; A61M 2205/6018; G01D 5/12; G01D 5/125; G01D 5/16; G01D 5/165; G01D 5/1655; G01D 5/25; G01D 5/251; G01D 5/2515; G01D 5/252; G01D 5/2525; G16H 20/17

See application file for complete search history.

(56) References Cited

U.S. PATENT DOCUMENTS

| | | | |
|---|---|---|---|
| 2011/0213306 A1* | 9/2011 | Hanson | A61M 5/1413 604/151 |
| 2014/0148763 A1 | 5/2014 | Karlsson et al. | |
| 2017/0124284 A1* | 5/2017 | McCullough | A61M 5/31568 |

FOREIGN PATENT DOCUMENTS

| | | |
|---|---|---|
| CN | 102413855 A | 4/2012 |
| WO | 2007/107558 A2 | 9/2007 |
| WO | 2010/098927 A1 | 9/2010 |

* cited by examiner

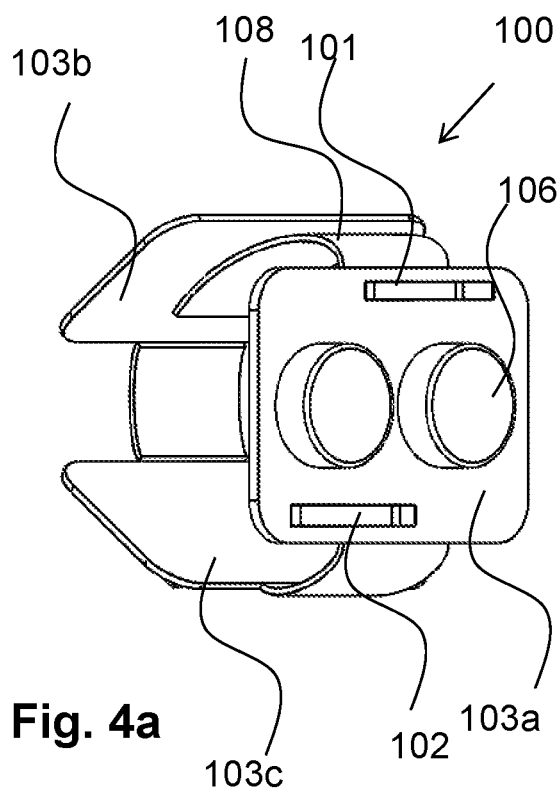
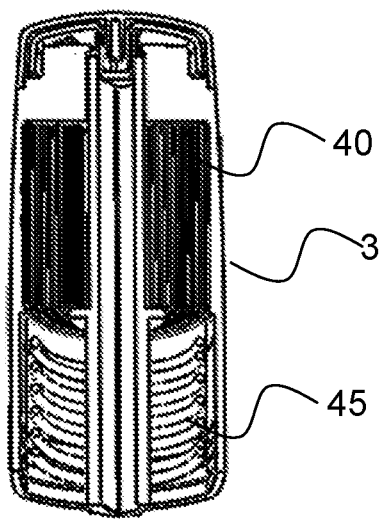
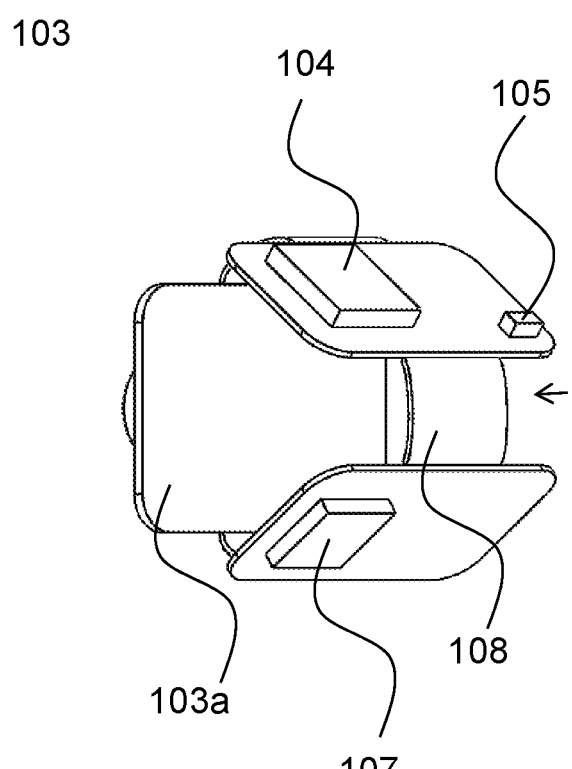
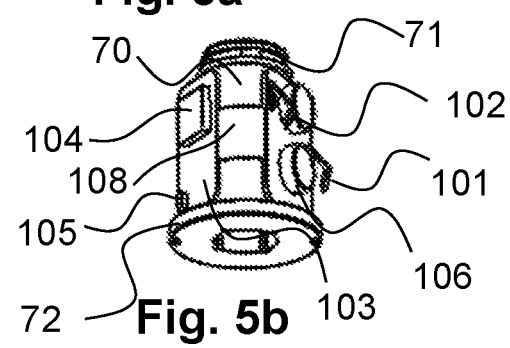
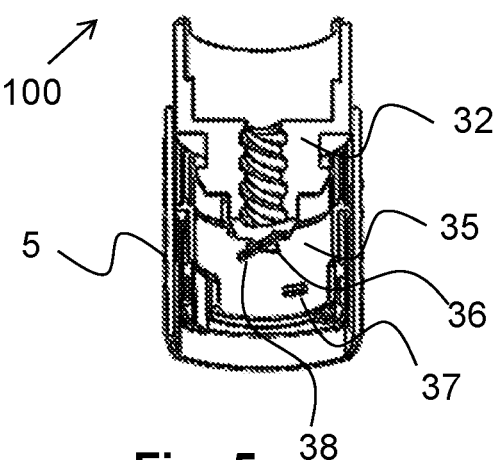
Fig. 4a
Fig. 4b
Fig. 5a
Fig. 5b
Fig. 5c

COMMUNICATION DEVICE FOR TRANSMITTING INFORMATION FROM A MEDICAMENT DELIVERY DEVICE

CROSS REFERENCE TO RELATED APPLICATIONS

The present application is a U.S. National Phase Application pursuant to 35 U.S.C. § 371 of International Application No. PCT/EP2016/077805 filed Nov. 11, 2016, which claims priority to European Patent Application No. 15202193.7 filed Dec. 22, 2015. The entire disclosure contents of these applications are herewith incorporated by reference into the present application.

TECHNICAL FIELD

The present disclosure relates to a communication device as defined in the preamble of claim 1.

BACKGROUND

The following background information is a description of the background of the present disclosure, which thus not necessarily has to be a description of prior art.

Medicament delivery devices, such as for example injection devices, auto-injection devices or pen-injection devices, are nowadays commonly used for helping patients to take their medicaments/drugs. Other medicament delivery devices could further be inhalers, eye dispense, or gel dispensers. Such medicament delivery devices may have one or more automatic functions providing/facilitating the delivery of the medicaments, such as for example automatic penetration, automatic retraction, and/or automatic injection. Such medicament delivery devices may also have one or more safety arrangements for preventing from accidental needle sticks, such as automatic needle guards and/or activation/trigger buttons enabling/disabling injection.

The medicament delivery devices can e.g. be activated by pressing the device against a body part. The device can then be pressed against the body part for example by the patient and/or by trained personnel, such as physicians or nurses. The medicament delivery devices often comprise a housing, a spring acting on a plunger rod, which in its turn acts on a stopper inside a medicament container for expelling the medicament through a needle attached to the container when being pressed against the body part. Hereby, an automatic or semiautomatic delivery of the medicament is provided by the device.

Medicament delivery devices help patients taking their medicaments. Especially, the right dosage of the medicament is secured by use of the device itself, since the amount of medicament/drug in the medicament container can be set/chosen to correspond to the prescribed dose. Normally, the medicament delivery device is essentially completely emptied by the delivery, whereby the prescribed dose of medicament is injected to the patient.

However, the adherence/compliance to take the medicaments according to a prescribed scheme over time is poor for some patients and/or patient groups. There can be many reasons for such non-compliance. One reason can be that the patient is in pain and/or that the delivery of the medicament itself is unpleasant, or maybe even painful. Another reason can be that the patient simply forgets to take the medicament. It should be noted that some sicknesses/diseases/conditions and/or medicaments affect the ability to remember things, and therefore increase the risk for the patient to forget taking the medication.

When the patient does not follow the prescribed medication scheme, there is a risk that the sickness/disease/condition is prolonged or worsened, and/or that the patient is stricken with further complications. A prolonged or worsened sickness/disease/condition and/or further complications of course adds both to the suffering of the patient and to the total costs for the medicaments and medical care. Therefore, medical care personal treating the patient, as well as authorities and/or insurance companies paying for the treatment, want to be able to monitor the intake of medicaments for the patient.

Today, the intake of the medicaments can be estimated based on a count of how many of the prescriptions having been made up for a patient that are actually collected by the patient at e.g. a pharmacy. This is, however, a very uncertain method, since it is not at all guaranteed that a collected medicament is also taken by the patient.

The intake of medicaments can today also be monitored by the use of applications/computer programs, in which the patient can enter data after each time a medicament dose has been taken. However, the probability that patients being likely not to take the medicament would remember and/or go through the extra work to enter data into such applications/computer programs is low. Thus, the information gathered by such applications/computer programs is very unreliable. Also, it is not at all certain that a missed entry in the application/computer program means that the medicament has not been taken. It is also not guaranteed that an entry in the application/computer program means that the medicament was taken.

SUMMARY

It is therefore an object to solve at least some of the above mentioned disadvantages and to provide a device which facilitates reliable monitoring of that patients follow their prescribed medication scheme, i.e. that the patients take the prescribed dose at the prescribed time instants.

The object is achieved by the above mentioned communication device according to the characterizing portion of claim 1.

According to an aspect of the present disclosure, a communication device arranged for transmitting information from a medicament delivery device is presented.

The communication device includes at least one translation detection arrangement, configured to detect a translation of at least one physical part of the medicament delivery device by utilization of a resilience and an electrical conductivity for at least one spring of the medicament delivery device.

The communication device also includes at least one change of state detection unit, configured to detect at least one change of state for the medicament delivery device based on the detected translation.

The communication device further includes at least one activation unit, configured to activate the at least one change of state detection unit based on the at least one detected translation.

The communication device also includes at least one transmission unit configured to provide a wireless transmission of information related to the at least one change of state to an external receiving device.

By usage of the present disclosure, the suffering of the patients can be minimized. Also, the overall cost for medical care can be lowered for some patients and/or patient groups.

The at least one change of state can e.g. be used as a distinct indication that the medicament delivery device is activated. The activation of the medicament delivery device is an indication that the medicament is taken by the patient. Therefore, the present disclosure provides for automated and reliable monitoring of whether patients follow their prescribed medication schemes or not. Based on this monitoring, e.g. a doctor treating a patient can directly contact a patient not following the medication scheme to hear what the problem is. Thus, the monitoring could help a doctor to find out which of his patients that need additional information and/or help with taking the medicaments. Maybe, the doctor could also come to the conclusion that a change of medicament should be made in order to increase the compliance of the patient, e.g. if the prescribed medicament is unpleasant/uncomfortable for the patient to take.

Also, authorities and/or insurance companies paying for the medical care can, based on the monitoring, contact the patient to inform the patient that they will stop paying for the treatment if the patient does not follow the prescribed medication scheme. An insurance company could also use the monitoring for adjusting the pricing level of a health care insurance for the patient.

The present disclosure can thus be used for improving the compliance to a prescribed medication scheme, which lowers the risk for a prolonged sickness/disease/condition and/or lowers the risk that the patient is stricken with further complications. Hereby, the suffering for the patient is minimized, and the total costs for the medicaments and medical care are also lowered.

According to an embodiment of the present disclosure, the communication device includes a first connector and a second connector; and at least one of the first connector and the second connector is insulated from electrical contact with the at least one spring when the at least one spring is in a compressed form.

According to an embodiment of the present disclosure, the electrical insulation is caused by one in the group of:
at least one electrically insulating part of said medicament delivery device being positioned between the at least one spring and at least one of the first connector and the second connector;
a physical isolation of the at least one spring from at least one of the first connector and the second connector; and
—at least one insulating strip being positioned between the at least one spring and at least one of the first connector and the second connector.

According to an embodiment of the present disclosure, the communication device includes a first connector and a second connector; and both of the first connector and the second connector are in electrical contact with the at least one spring when the at least one spring is in an expanded form, thereby creating a closed circuit via the at least one spring.

According to an embodiment of the present disclosure, the at least one spring has one form in the group of:
a compressed form during a first state for the medicament delivery device;
an expanded form during a second state for the medicament delivery device;
an expanded form during a first state for the medicament delivery device; and
a compressed form during a second state for the medicament delivery device.

According to an embodiment of the present disclosure, the at least one spring is in the second state during and after a medicament delivery performed by the medicament delivery device.

According to an embodiment of the present disclosure, the at least one spring, in combination with the first connector and the second connector, is configured to function as a translation switch, the translation switch being activated by a translational movement of the at least one physical part of the medicament delivery device.

According to an embodiment of the present disclosure, the first connector and the second connector are arranged according to at least one in the group:
at least one of the first connector and the second connector is arranged on an inside of the at least one spring; and
at least one of the first connector and the second connector is arranged on an outside of the at least one spring.

According to an embodiment of the present disclosure, the communication device is included in an external unit being releasably attachable to the medicament delivery device; and the first connector and the second connector are coupled to the external unit by a first conductor and a second conductor, respectively.

According to an embodiment of the present disclosure, the communication device is integrated in a housing of the medicament delivery device.

According to an embodiment of the present disclosure, the at least one spring includes at least one in the group of:
an injection spring configured to cause an injection of a medicament;
a penetration spring configured to move a medicament container and a needle attached to the medicament container towards a proximal end of the medicament delivery device;
a retraction spring configured to move a medicament container and a needle attached to the medicament container distally from a proximal end of the medicament delivery device;
a needle guard spring configured to urge/bias a needle guard sleeve towards a proximal end of the medicament delivery device; and
a trigger button spring configured to urge/bias a trigger button towards a distal end of the medicament delivery device.

According to an embodiment of the present disclosure, the at least one spring is arranged as one in the group of:
at least one combined spring providing functions corresponding to two or more springs; and
separate springs, each providing a function corresponding to one of the at least one spring.

According to an embodiment of the present disclosure, the information related to the medicament delivery is based on preconfigured data and/or measured data, the data including one or more in the group of:
an identification number for the medicament delivery device;
an identification number for a drug being delivered by the medicament delivery device;
an identification number for a patient using the medicament delivery device;
an elapsed time since a delivery of a drug occurred; and
at least one detected change state, wherein each state represents one step in a sequence of steps of a medicament delivery.

According to an embodiment of the present disclosure, the communication device further includes at least one indication unit configured to provide at least one indication of that the medicament delivery is performed, the at least one indication being provided during the delivery and also during a predetermined time period after the delivery has ended.

According to an embodiment of the present disclosure, the communication device further includes at least one indication unit including one or more in the group of:

- at least one light source configured to emit light as the at least one indication; and
- at least one light guide configured to guide light being emitted by at least one light source as the at least one indication.

The above mentioned units, such as the at least one translation detection arrangement, the at least one change of state detection unit, the at least one activation unit, the at least one determination unit, the at least one indication unit and/or the at least one transmission unit can be at least partly implemented in a computer program, which, when it is executed in a processor, instructs the processor to execute the steps taken by the units, respectively. The computer program is often constituted by a computer program product stored on a non-transitory/non-volatile digital storage medium, in which the computer program is incorporated in the computer-readable medium of the computer program product. Said computer-readable medium comprises a suitable memory, such as, for example: ROM (Read-Only Memory), PROM (Programmable Read-Only Memory), EPROM (Erasable PROM), Flash memory, EEPROM (Electrically Erasable PROM), a hard disk unit, etc.

Here and in this document, the arrangements and/or units are often described as being arranged for performing steps according to the disclosure. This also includes that the units are designed to and/or configured to perform these steps. For example, these units can at least partly correspond to groups of instructions, which can be in the form of programming code, that are input into, and are utilized by the processor when the units are active and/or are utilized for performing its step, respectively.

Detailed exemplary embodiments and advantages of the communication device according to the disclosure will now be described with reference to the appended drawings illustrating some preferred embodiments.

BRIEF DESCRIPTION OF THE DRAWINGS

Embodiments of the disclosure are described in more detail with reference to attached drawings illustrating examples of embodiments of the disclosure in which:

FIGS. 4a-b show a communication device according to some embodiments, FIGS. 5a-c show parts of a medicament delivery device and of a communication device according to some embodiments.

DETAILED DESCRIPTION

In the following, the present disclosure is often exemplified as implemented in an injection device. The present disclosure can, however, be implemented in essentially all kinds of medicament delivery devices that include at least one physical part which providing a translational movement when a state of change occurs in the medicament delivery device, e.g. when the medicament delivery device is enabled for activation, is activated, delivers the medicament to the patient, and/or the medicament delivery device protects the device from accidental activation or protects the user from the needle. The medicament delivery device according to the present disclosure is thus not restricted to implementation in injection devices.

Figure 1A:
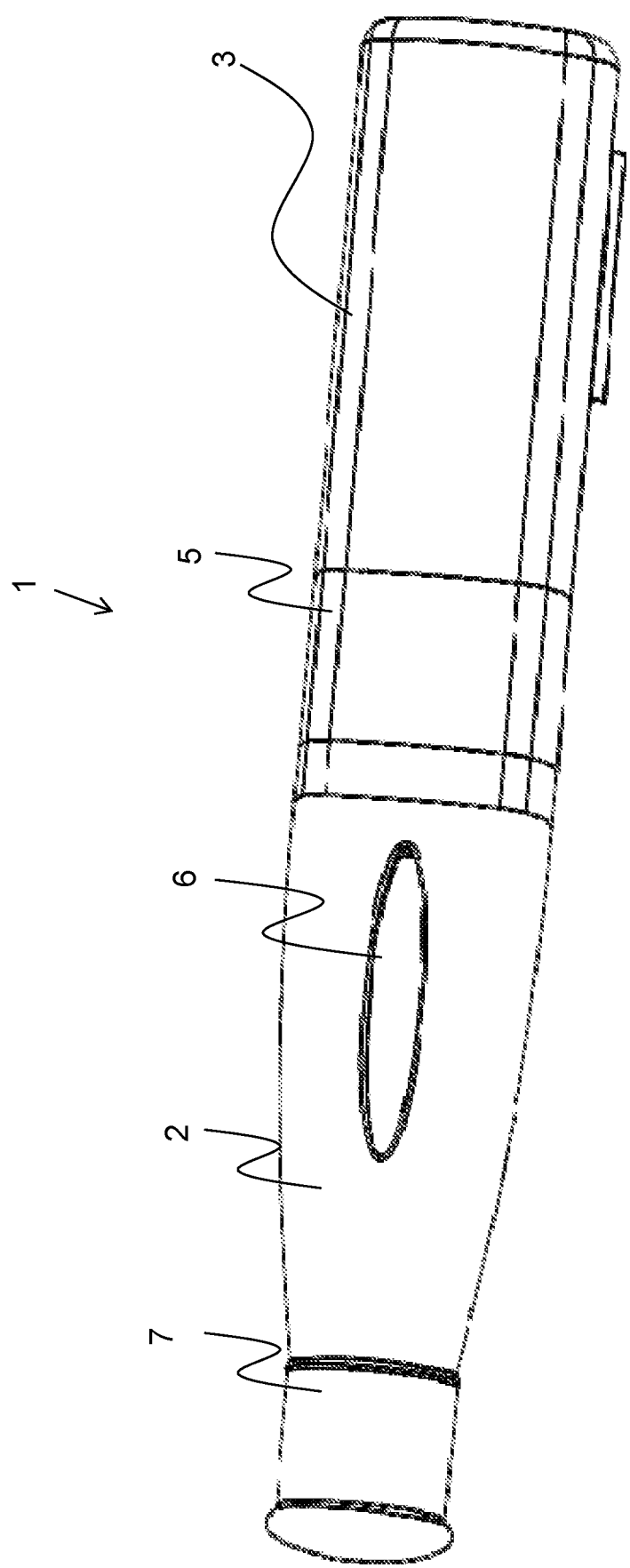
FIGS. 1a-c show a medicament delivery device.
Figure 1B:
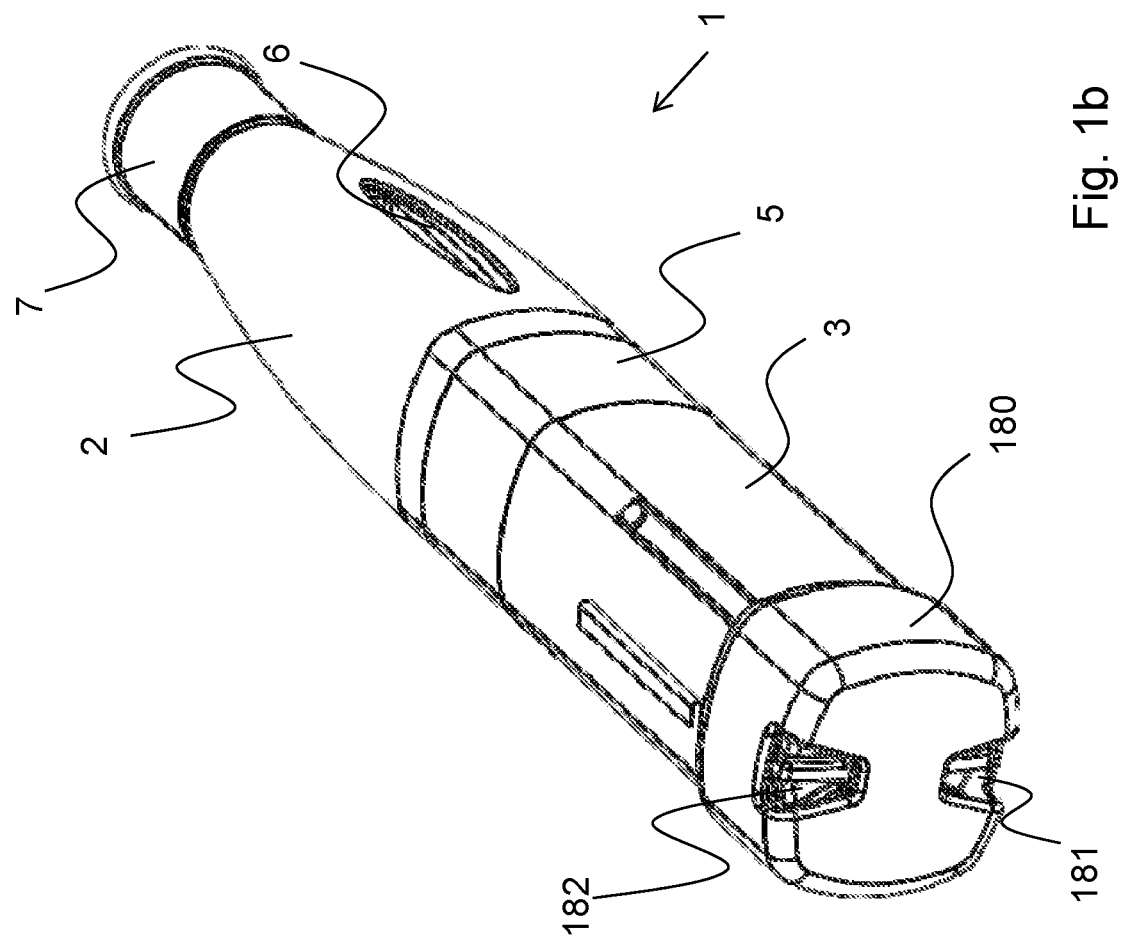
Figure 1C:
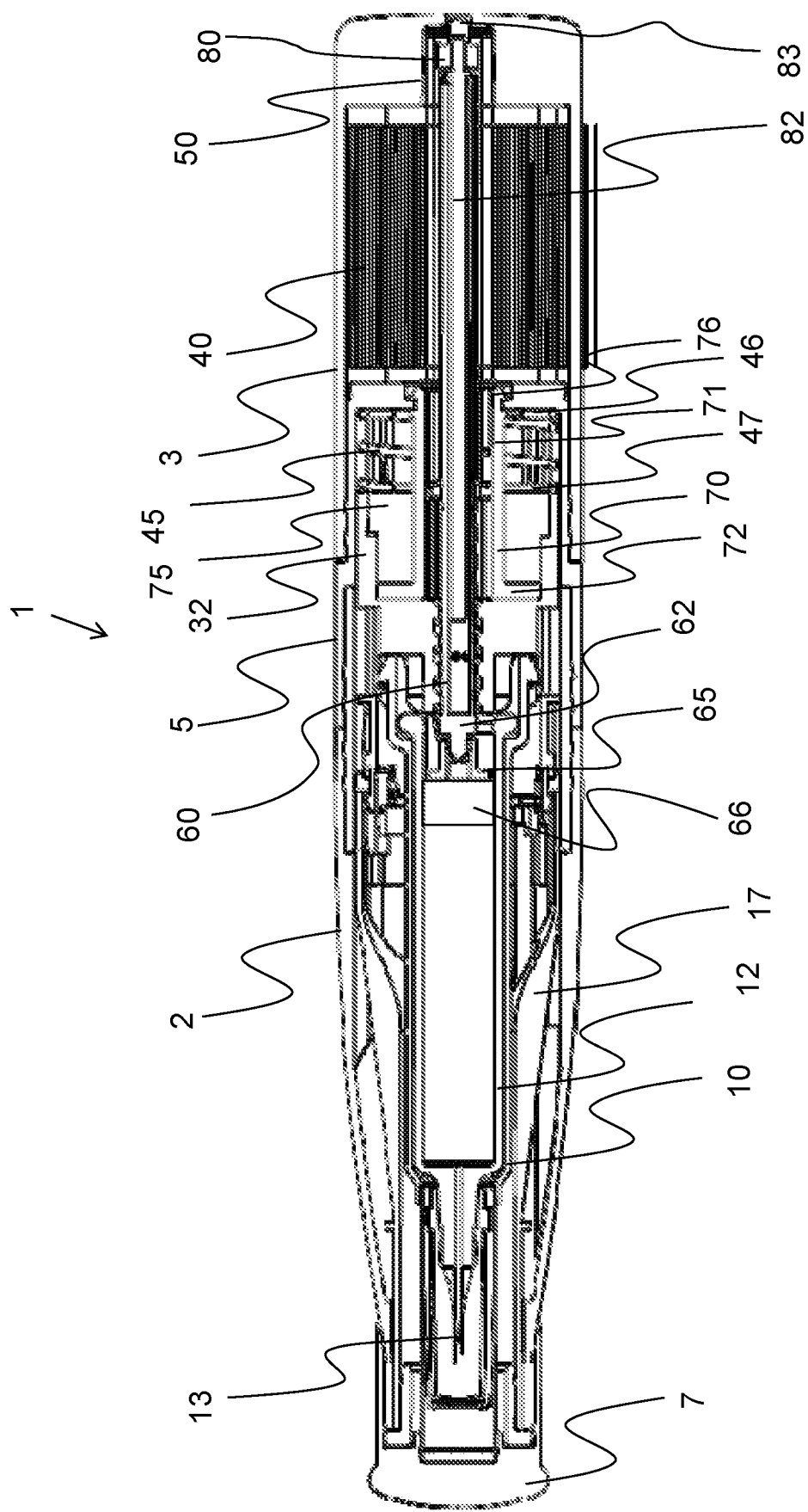

In FIGS. 1a-c, a non-limiting example of a medicament delivery device 1 is shown. In FIGS. 1a-c, the same components are labeled with identical reference numerals.

FIG. 1a shows a perspective view of an injection device 1, in which the communication device according to the present disclosure can be implemented. The injection device 1 has a housing that comprises a proximal housing part 2, a distal housing part 3, a proximal intermediate housing part (not shown in FIG. 1a), and a distal intermediate housing part 5. In the assembled state of the injection device 1, the proximal housing part 2, the distal housing part 3, and the distal intermediate housing part 5 form the outer surface or appearance of the injection device 1.

In this document, when the term "distal" is used, this refers to the direction pointing away from the dose delivery site. When the term "distal part/end" is used, this refers to the part/end of the delivery device, or the parts/ends of the members thereof, which is/are located furthest away from the dose delivery site. Correspondingly, when the term "proximal" is used, this refers to the direction pointing to the dose delivery site. When the term "proximal part/end" is used, this refers to the part/end of the delivery device, or the parts/ends of the members thereof, which is/are located closest to the dose delivery site.

As shown in FIG. 1a, the proximal housing part 2 comprises at least one window 6, which allows the user to view the state of the injection, i.e. whether the injection device 1 is still in its initial stage with the medicament not yet being injected, or whether the medicament container is already emptied. Through window 6, the user can see the medicament container accommodated at least in the proximal housing part 2. FIG. 1a also shows a front cap 7, which closes the proximal opening of the proximal housing part 2 until the injection device 1 is used.

FIG. 1b shows a perspective view of the injection device 1 shown in FIG. 1a. As shown in FIG. 1b, the injection device 1 can include an indicator assembly 180. The indicator assembly comprises a cap having at least one opening 181. Through this opening 181, the user can see a signaling element in the form of a rotatable wheel or disk 182. The wheel or disk 182 is rotated when the medicament is delivered to the patient, thereby indicating that an injection is taking place. As is understood by a skilled person, the indicator assembly 180 can have a large number of forms and/or features.

FIG. 1c shows some, not all, internal parts of the injector illustrated in FIGS. 1a-b. A medicament delivery device includes a large number of internal parts. In this document, however, only the parts of a medicament delivery device, exemplified by an injector, being essential for understanding the present disclosure are described. For a more complete description of the injector parts, and their functions, reference is made to document US2014/0148763.

FIG. 1c shows a sectional view of the injection device 1 in its initial position, i.e. before the medicament has been injected.

The injection device 1 includes a needle 13, FIG. 1c, of a medicament container 12 being covered by a rigid needle shield 17. A plunger driver 50 is initially, i.e. before injection, rotationally locked to a plunger drive locking member 70, but is slidable in axial direction in relation to plunger drive locking member 70. The plunger rod 60 may comprise a threaded structure as well as at least one longitudinal groove. At the proximal end, the plunger rod 60 comprises a plunger rod tip 62 onto which a spinner element 65 can be attached by snap fit. The spinner element 65 acts on a stopper 66 in the medicament container 12 in order to deliver the medicament.

In the initial stage of the injection device 1, i.e. prior to its use, a proximal part of the plunger rod 60 is received in the central opening of the container driver 32. However, once the plunger drive locking member 70 is free to rotate, which happens when the injection starts, the plunger driver 50 and the plunger rod 60 also start to rotate, caused by a first spring 40. The plunger drive locking member 70 has essentially a cylindrical form, and possibly also has a locking member 76 at its distal end 71. The plunger driver locking member 70 also has a flange/stop wheel 72 at its proximal end.

Furthermore, FIG. 1c shows a first energy accumulating member, e.g. a first spring 40, which is used to perform an injection, and a second energy accumulating member, e.g. a second spring 45, herein also called penetration spring 45, which is used to axially move the medicament container holder 10 in order to perform a needle penetration prior to injection of the medicament.

The medicament container holder 10 is connected with the container driver 32, and a longitudinal displacement of the container driver 32 towards the proximal end of the injection device 1, caused by the penetration spring 45, results in a movement of the medicament holder 10 towards the proximal end of the injection device 1, whereby a needle penetration is performed.

FIG. 1c further shows how the second spring 45 is located in the interior of the distal intermediate housing part 5. The distal end 46 of the second spring 45 is in contact with the inner surface of the distal radial wall of the distal intermediate housing part 5. Alternatively, it may be in contact with a ledge provided at the inside of the distal intermediate housing part, proximal to the distal radial wall of the distal intermediate housing part 5. The proximal end 47 of the second spring 45, on the other hand, abuts against a distal surface of the container driver 32.

The injection device may further comprise a needle shield sleeve or guard 17 arranged slidable in a proximal part of the housing and being capable of acting on a container driver locking member when said needle shield sleeve 17 is pressed against an injection site. The needle shield sleeve 17 initially covers the needle 13 of the medicament container.

The needle shield sleeve 17 according to an embodiment of the present disclosure is movable or displaceable. After the device has been used, the needle shield sleeve 17 is moved and locked in a distal position when the device is withdrawn from the dose delivery site. The needle shield sleeve 17 is then preferably urged in a proximal direction by the force of at least one spring, i.e. the herein denoted needle guard spring. The spring(s) may be provided at the distal end of the needle shield sleeve 17. Thus, the needle shield sleeve 17 is a protection element, such as a needle protection element or needle protection sleeve that protects the user against inadvertently or accidentally getting in contact with the needle which may be contaminated.

As described above, the needle 13 is covered or retracted until the injection device is actuated and may not be unintentionally contacted until this moment. The needle shield sleeve 17 is movable between a proximal and a distal position. The needle shield sleeves 17 is preferably contacted and moved when the injection device is positioned at the injection site. On the other hand, the removable front cap 7 at the proximal opening of the housing prevents the needle shield sleeve 17 from being accidentally moved prior to use of the device.

The proximal part of needle shield sleeve 17 is preferably of generally cylindrical form (assuming generally cylindrical shape of the medicament container). The most proximal part is a fully closed cylinder, and extends from the proximal end of the needle shield sleeve a certain distance towards the distal end of the injection device. The needle shield sleeve 17 can for example have a widening configuration in that it widens from the proximal end towards the distal end thereof.

As stated above, the needle guard spring, is used for urging the needle shield sleeve or guard 17 towards the proximal end of the injection device when the injection device is removed from the injection site. Thus, the needle shield sleeve 17 preferably covers the needle when the injection device is withdrawn from the injection device.

The injection device may further comprise a locking member for locking the needle shield sleeve 17 against moving towards the distal end of the injection device when the injection device is removed from the injection site. When the user removes the injection device from the injection site, the needle shield sleeve 17 is urged towards the proximal end of the injection device. The needle shield sleeve 17 is then locked at the proximal end by suitable locking structures.

When the injection device 1 is placed on an injection site, for example the skin of a user, the needle shield sleeve 17 is thereby pushed or moved towards the distal end of the injection device 1. Thus, a longitudinal displacement of the needle shield sleeve 17 towards the distal end of the injection device 1 is provided. As long as the injection device is pressed on the injection site, the needle shield sleeve 17 is held in its distal position. However, when the user removes the injection device 1 from the injection site, for example after medicament delivery, the needle shield sleeve 17 is urged towards the proximal end of the injection device 1, as described above. During this movement, the needle shield sleeve is locked at the proximal end, which prevents that the needle shield sleeve 17 can again be moved towards the distal end of the injection device 1.

A central opening of the container driver 32 comprises a threaded structure that engages with the threads of the plunger rod 60. Thus, the threaded proximal section of the plunger rod 60 is screw threaded in the interior of the container driver 32. Due to this threaded engagement, rotation of the plunger rod 60 upon use of the injection device results in an axial displacement of the plunger rod 60 towards the proximal end of the injection device. In other words, the plunger rod 60 is rotated by the threaded engagement in the direction of the medicament container 12, and causes the stopper 66 in the medicament container 12 and in abutment with spinner 65 to move towards the proximal end of the medicament container 12 in order to expel medicament through the injection needle 13.

When the plunger rod 60 is proximally advanced, during the injection, the indicator 80 and the indicator rod 82, being part of the indicator assembly, are forced distally. The plunger rod 60 is then also rotationally locked to the plunger driver 50 but may axially slide along ribs of the plunger driver 50. The plunger driver 50 is connected to the inner end of a first spring 40, whereby a force applied to the plunger driver 50 by the first spring 40 is transmitted to the plunger rod 60. Thus, the plunger driver 50 is rotated by the first spring 40 when the medicament is expelled/injected.

The force of the first spring 40 will continue to drive the plunger rod 60 towards the proximal end of the injection device 1, thereby pressing the stopper 66 to expel medicament through the needle 13. The injection is completed when the stopper 66 is at the proximal end of the medicament container 12.

When the plunger rod 60 is fully rotated towards the proximal end of injection device 1, a compression spring (not shown) coaxially arranged with the indicator rod 82 causes the indicator assembly to move distally until the indicator 80 contacts the distal front surface of the distal housing part 3. This causes the distal protrusion of the indicator 80 to project through an indicator opening 83 provided in the centre of the distal wall of the distal housing part 3. This provides a visible and tactile indication to the user that the complete dose has been expelled.

As mentioned above, the communication device according to the present disclosure may be implemented in a large number of different medicament delivery devices. The injector illustrated in FIGS. 1a-c is only one non-limiting example of such medicament delivery devices.

According to an aspect of the present disclosure, a communication device arranged for transmitting information from a medicament delivery device is presented.

The communication device includes at least one translation detection arrangement, which is configured to detect a translation of at least one physical part of the medicament delivery device. When e.g. a medicament delivery is performed by the medicament delivery device, one or more physical parts of the medicament delivery device perform a translation movement, i.e. a longitudinal/axial movement in a distal and/or proximal direction. As mentioned above, e.g. the plunger driver 50, the spinner element 65, the stopper 66 in the medicament container 12, the medicament container holder 10, the needle 13, the container driver 32, plunger rod 60, the indicator 80 and/or the indicator rod 82 are moved axially when a needle penetration and/or an injection is performed. Also, e.g. the needle shield sleeve 17 is axially moved when the medicament delivery device 1 is pressed against the skin, or is removed from the skin. In addition to these above mentioned movements, further physical parts of the medicament delivery device 1 may also move axially when the medicament delivery device is activated.

According to the present disclosure, any such translations of at least one physical part of the medicament delivery device is detected by utilization of a resilience and an electrical conductivity for at least one spring of the medicament delivery device 1. As mentioned above, the medicament delivery device may include one or more springs causing and/or being part of such translation/axial movements. Such springs may according to the present disclosure be used for detection of translations/axial movements.

The communication device further includes at least one change of state detection unit, configured to detect at least one change of state for the medicament delivery device 1 based on the detected translation. In other words, if a translational movement is detected, a change of state can thereby be detected according to the present disclosure.

The at least one change of state detection unit is here activated by at least one activation unit based on the at least one detected translation/axial movement. Thus, the at least one change of state detection unit will be activated when a translation is detected, e.g. when a medicament delivery is performed.

The medicament delivery device also includes at least one transmission unit being configured to provide a wireless transmission of information related to the at least one change of state to an external receiving device. The transmission may be performed in essentially any format being suitable for transfer of data wirelessly, such as according to for example a Bluetooth transmission protocol or another similar short range transmission protocols, or according to a cellular communication protocol of some kind. The external receiving device can be essentially any device including a receiver, such as for example be a portable device, such as a tablet, a smartphone or a laptop, or a stationary device, such as a stationary computer, a server equipment, a router equipment or a network hub.

According to different embodiments of the present disclosure, the at least one activation unit is configured to activate the at least one change of state detection unit and/or the at least one transmission unit based on the detected translation. According to an embodiment, the whole communication device 100 is activated by the at least one activation unit when a translation is detected.

According to an embodiment, the communication device also includes at least one determination unit configured to determine information related to a medicament delivery performed by the medicament delivery device. The information can be based on preconfigured data and/or measured data related to the medicament delivery. Such data may include e.g. an identification number identifying the medicament delivery device, an identification number identifying a medicament/drug being delivered by the medicament delivery device, an identification number identifying a patient using the medicament delivery device, and/or an elapsed period of time since a delivery of a medicament/drug occurred.

Such data may also include at least one detected change of state. A medicament delivery sequence includes a number of steps. As is described above, a number of parts of the medicament delivery device, such as e.g. springs, drivers, rotators, sleeves, rods and indicators, are activated when a medicament is delivered to the patient. These parts are activated in a specific sequence in order for the medicament delivery device to work properly. When the sequence proceeds from one step to a subsequent step, a change of state can occur, i.e. each state can represent one step in a sequence of steps of a medicament delivery, and corresponding change of state can be performed when the sequence proceeds from one sequence step to the next. If such changes of states are detected and reported, a producer/manufacturer/seller of the medicament delivery devices may use this information to monitor the usage and/or the function of device. For example, if the steps of the sequence are detected and/or reported in an correct order being incorrect, a malfunction of the medicament delivery device may be detected. Also, if the steps of the sequence are detected and/or reported in an incorrect order, it can be concluded that the medicament delivery device is handled incorrectly by the user. Thus, an analysis of the detected and/or reported steps, i.e. of the detected and/or reported changes of states, in comparison with an expected sequence of steps, i.e. with an expected sequence of changes of states, for a medicament delivery device, can reveal if the device is malfunctioning and/or is incorrectly used.

Figure 2A:
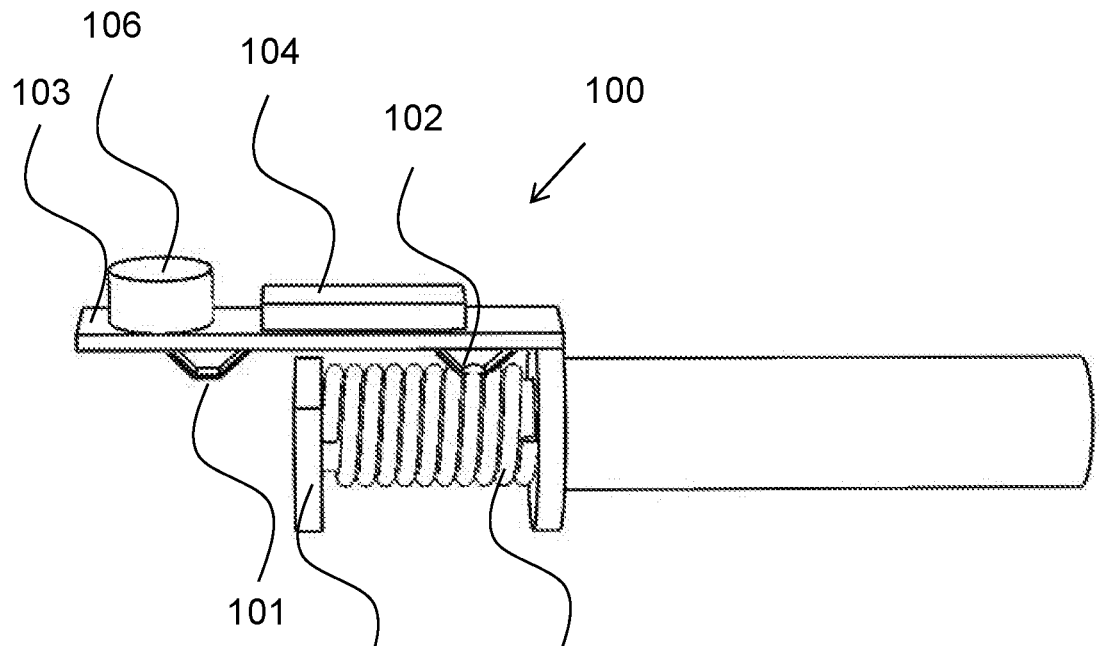
FIGS. 2a-b schematically show a spring and a communication device according to some embodiments, FIGS. 3a-b schematically show a spring and a communication device according to some embodiments.
Figure 2B:
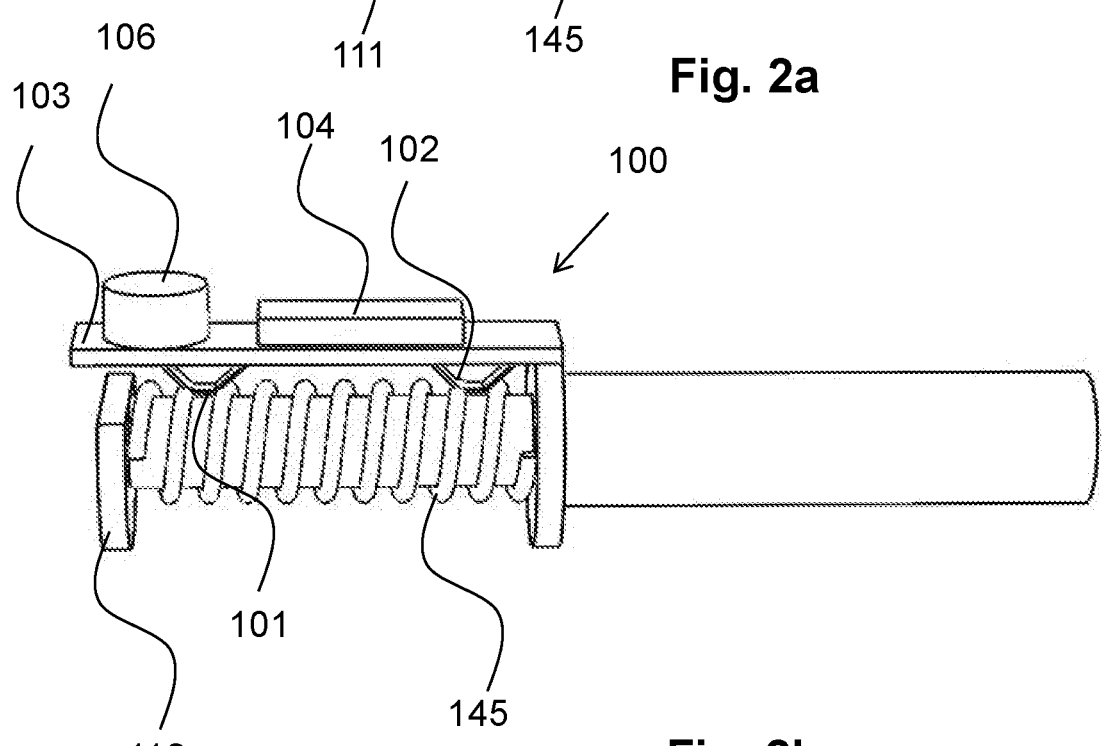

According to an embodiment of the present disclosure, which is schematically illustrated in FIGS. 2a-b in connection with expansion and compression of a spring 145 included in a medicament delivery device 1. The spring 145 in these figures can be essentially any spring included in a medicament device, and is here described in order to explain the principle of the embodiment.

As is shown in FIGS. 2a-b, the communication device 100 includes a first connector 101 and a second connector 102, possibly being mounted on a printed circuit board (PCB) 103. According to some embodiments, at least one processor 104, including at least one transmission unit, such as e.g. a Bluetooth transmission unit, can be arranged on the PCB 103 in order to transmit the information to the external receiver. The electronic circuits of the communication device 100 can be provided with electrical power by at least one battery 106 being arranged on the PCB 103.

At least one of the first connector 101 and the second connector 102, in the example of FIG. 2a the first connector 101, is insulated from electrical contact with the spring 145 when it is in a compressed form 111 in a first state for the medicament delivery device. The first state can for example be an initial state, before the medicament delivery device 1 has been activated to deliver medicaments. The first state can also be an intermediate state for the medicament delivery device 1 during the delivery of the medicament. The other one of the first connector 101 and the second connector 102, in the example of FIG. 2a the second connector 102, is in electrical/physical contact with the spring 145 in the first state. Since only one of the first connector 101 and the second connector 102 is in contact with the electrically conducting spring 145, an open circuit is created in the compressed mode/form of the spring 145, by the spring 145, the first 101 and second 102 connectors, possibly powered by the one or more batteries 106.

As is described more in detail below, the electrical insulation can here be caused by a physical isolation of the spring 145 from at least one of the first connector 101 and the second connector 102. In the example showed in FIG. 2a, the first connector 101 is separated from the spring 145 by air.

According to other embodiments, described more in detail below, at least one electrically insulating part of the medicament delivery device 1 is positioned between the spring 145 and at least one of the first connector 101 and the second connector 102 and/or at least one insulating strip is positioned between the spring 145 and at least one of the first connector 101 and the second connector 102.

As is illustrated in FIG. 2b, both of the first connector 101 and the second connector 102 are in electrical contact with the electrically conducting spring 145 when the spring 145 is in an expanded form 112 in a second state for the medicament delivery device. The second state can for example be an activated state, during and/or after the medicament delivery is performed. Thus, the second state can also be an intermediate state for the medicament delivery device 1 during the delivery of the medicament. Since both of the first connector 101 and the second connector 102 are in electrical contact with the spring 145, a closed circuit is created via the electrically conducting spring 145, possibly powered by the one or more batteries 106.

As is clear for a skilled person, the spring 145 could also be used in an opposite way, such that the spring 145 is in expanded form/mode during a first state for the medicament delivery device 1, and is in a compressed form/mode during a second state for the medicament delivery device 1. Thus, the spring 145 can have a compressed form 111 during a first state and an expanded form 112 during a second state for said medicament delivery device 1, or can have an expanded form 112 during a first state and a compressed form 111 during a second state for the medicament delivery device 1.

Thus, the communication device 100 according to the present disclosure uses at least one spring 145 in combination with its first connector 101 and its second connector 102, in order to achieve a function of a translation switch. The hereby created translation switch is then activated by a translational movement of the at least one physical part of the medicament delivery device 1, which causes a change of state detectable due to an opening or closing of the circuit including the at least one spring 145, the first connector 101 and the second connector 102.

As is schematically showed for the example embodiment in FIGS. 2a-b, both of the first connector 101 and the second connector 102 can be arranged on the outside of the spring 145, and are arranged such that they can come in contact with the spring.

Figure 3A:
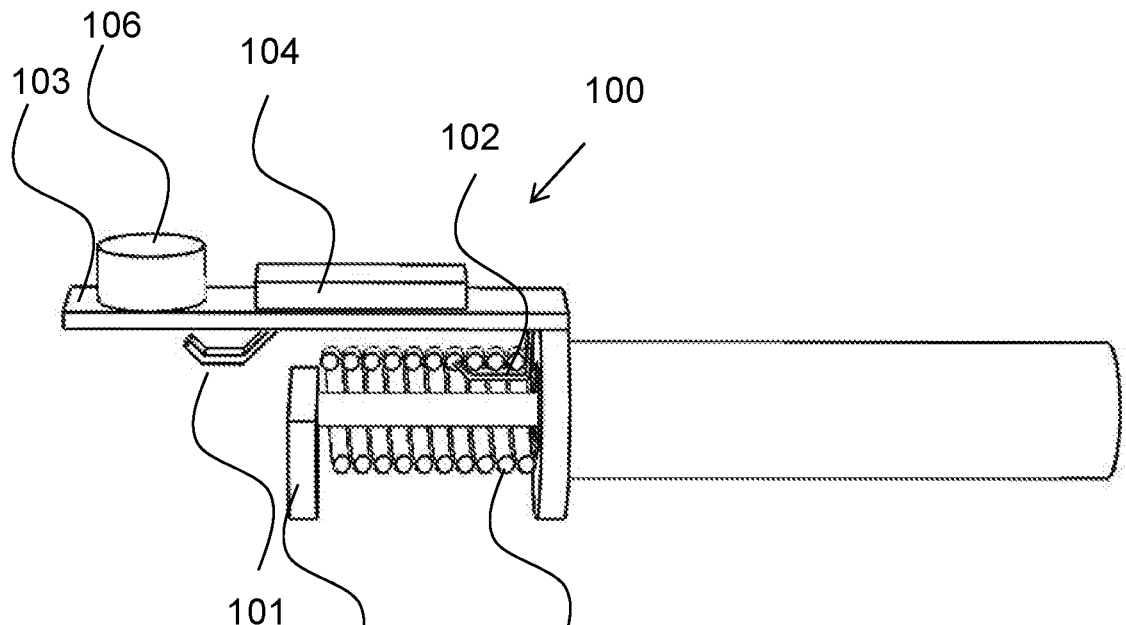
Figure 3B:
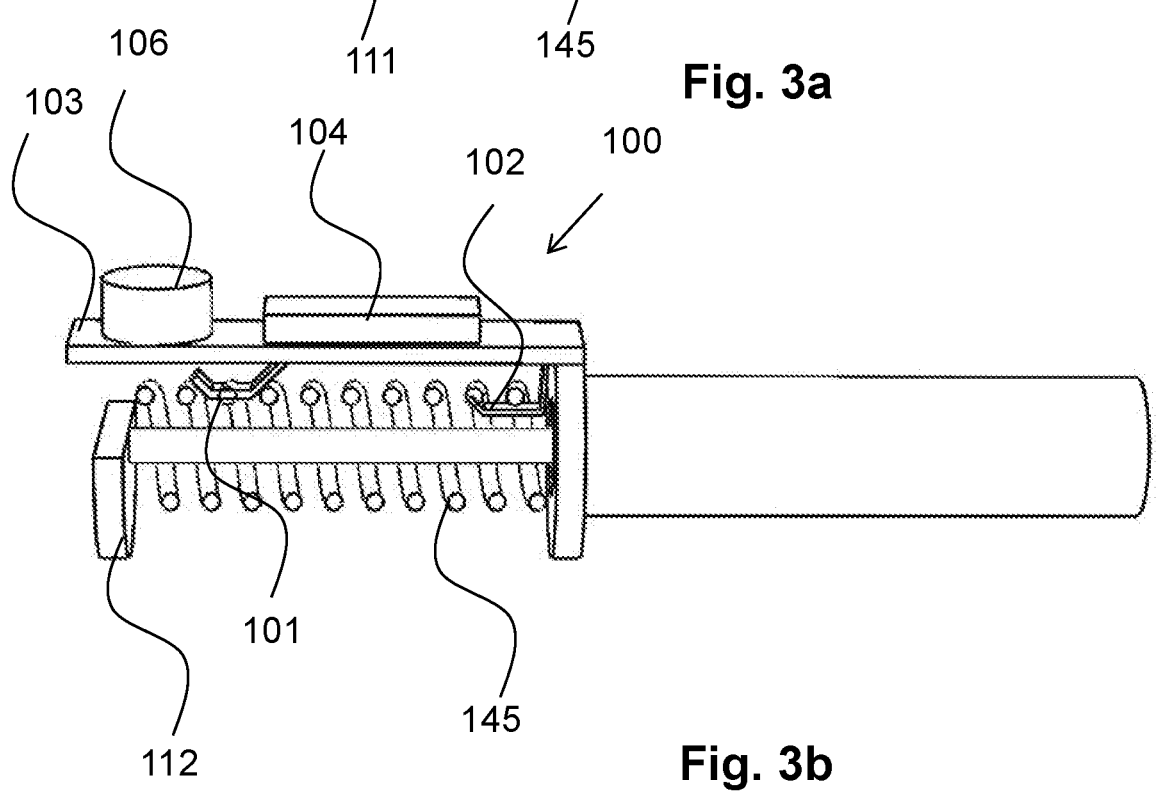

As is schematically showed for an example embodiment in FIGS. 3a-b, at least one of the first connector 101 and the second connector 102 can also be arranged on the inside of the spring 145, and is arranged such that it can come in contact with the spring. Otherwise, the communication device illustrated in FIGS. 3a-b functions as described above for FIGS. 2a-b. Thus, the first connector 101 is insulated from electrical contact with the spring 145 when it is in a compressed form 111 in a first state for the medicament delivery device. Then, both of the first connector 101 and the second connector 102 are in electrical contact with the electrically conducting spring 145 when the spring 145 is in an expanded form 112 in a second state for the medicament delivery device. Thus, the communication device 100 according to the present disclosure uses an opening or closing of a circuit including the spring 145 in combination with its first connector 101 and its second connector 102, in order to achieve a function of a translation switch being activated by a translational movement of at least one physical part of the medicament delivery device 1.

Thus, according to different embodiments, at least one of the first connector 101 and the second connector 102 is arranged on an inside of the at least one spring 145, and according to some embodiments, at least one of the first connector 101 and the second connector 102 is arranged on an outside of the at least one spring 145. The configuration of the springs as being inside and outside the spring 145, respectively, can depend on the constitution of the internal parts of the medicament delivery device, e.g. on the available space inside and outside the springs 145.

FIGS. 4a-b show a communication device 100 according to an embodiment of the present disclosure. According to the embodiment, the communication device 100 includes a number of PCBs 103a, 103b, 103c being attached to each other by a ring 108, which can be at least semi-flexible. The first 101 and second 102 connectors are mounted on the PCBs. Also, at least one processor/transmission unit 104 and at least one antenna unit 105 are mounted on the PCBs. According to an embodiment, the processor/transmission unit 104 is configured to create a connection between the communication device 100 and the external receiving device, e.g. a smartphone, essentially directly when a change of state has been detected, e.g. at the activation of one or more units of the communication device 100. The transmission unit 304 can also, as described in this document, be configured to transmit various information from the communication device 100 to the external receiving device. Hereby, interactive information may be presented e.g. by a smartphone during the medicament delivery.

According to an embodiment, at least one clock 107, such as e.g. a clock crystal device, can be configured to count a relative time related to the detected change of state, e.g. the delivery of drugs. Thus, the at least one clock 107 can then count the elapsed period of time from the occurred change of state, such as e.g. from the start of the medicament delivery, i.e. from the point in time when the change of state detection unit was activated. Hereby, the clock 107 may be in an off-mode until the determination unit is activated, which saves battery power for the at least one battery 106 providing electrical power for the communication device 100.

According to different embodiments of the present disclosure, the communication device 100 is integrated in a housing 2, 3, 5 of the medicament delivery device 1, as is disclosed in FIGS. 5a-c, 6a-b and 7a-b.

FIG. 5a shows a part of the housing 3 of the medicament delivery device, an injection spring 40 and a penetration spring 45. FIG. 5c shows a container driver 32 and a rotator 35 included in a part of the housing 5. The rotator 35 has a first/higher rest 36 and a second/lower rest 37, on which an actuator 38 can be supported, as described below.

FIG. 5b shows the communication device according to some embodiments of the present disclosure. The communication device 100 is arranged on the plunger drive locking member 70. Thus, the PCBs 103, the first 101 and second 102 connectors, the batteries 106, the processor/transmission unit 104, the antenna unit 105, and possibly also more units/arrangements described in this document, are fitted over the essentially cylindrical form of the distal end 71 and rests on the flange/stop wheel 72 at the proximal end of the plunger drive locking member 70.

FIGS. 5a-c show exploded views of parts of the medicament delivery device 1 and the communication device 100 according to the present disclosure. These parts can be assembled together, such that the communication device 100 is included within the housing 3, 5 of the medicament delivery device 1.

Figure 6A:
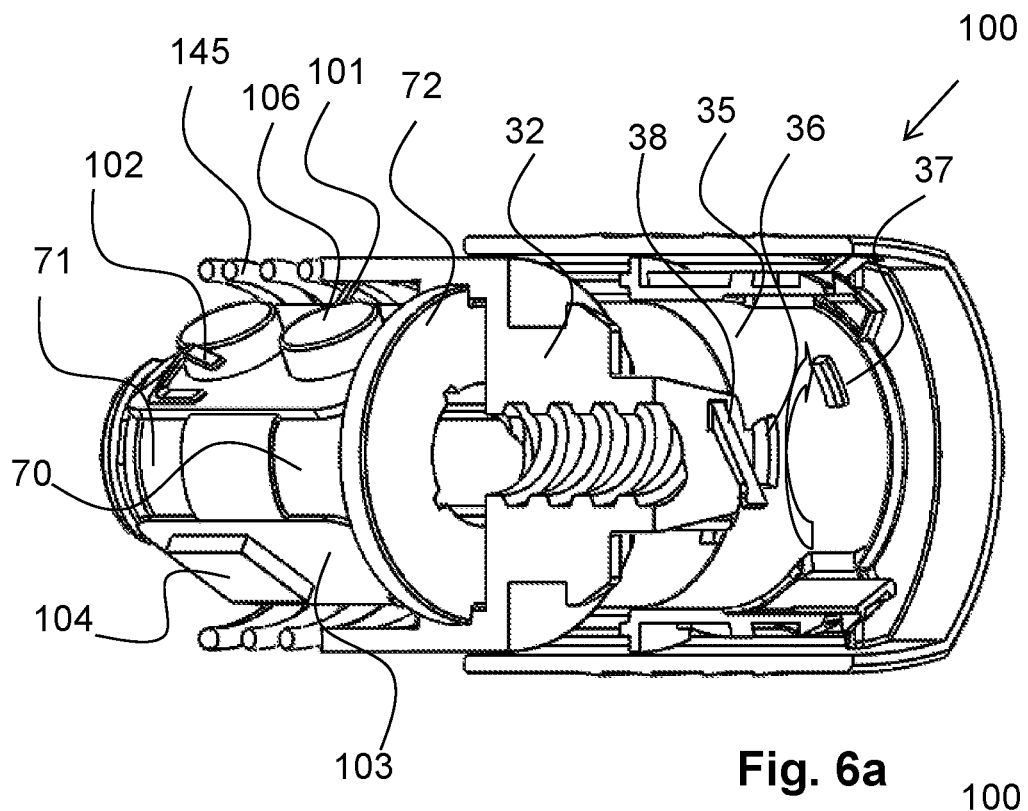
FIGS. 6a-b show parts of a medicament delivery device and of a communication device according to some embodiments.
Figure 6B:
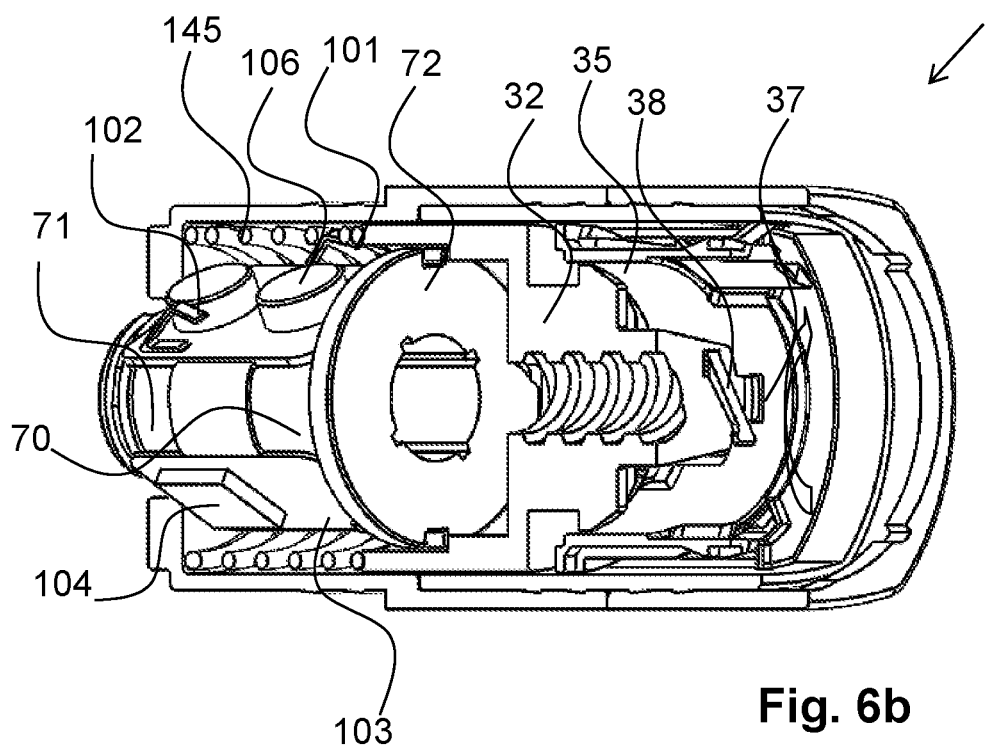
Figure 7A:
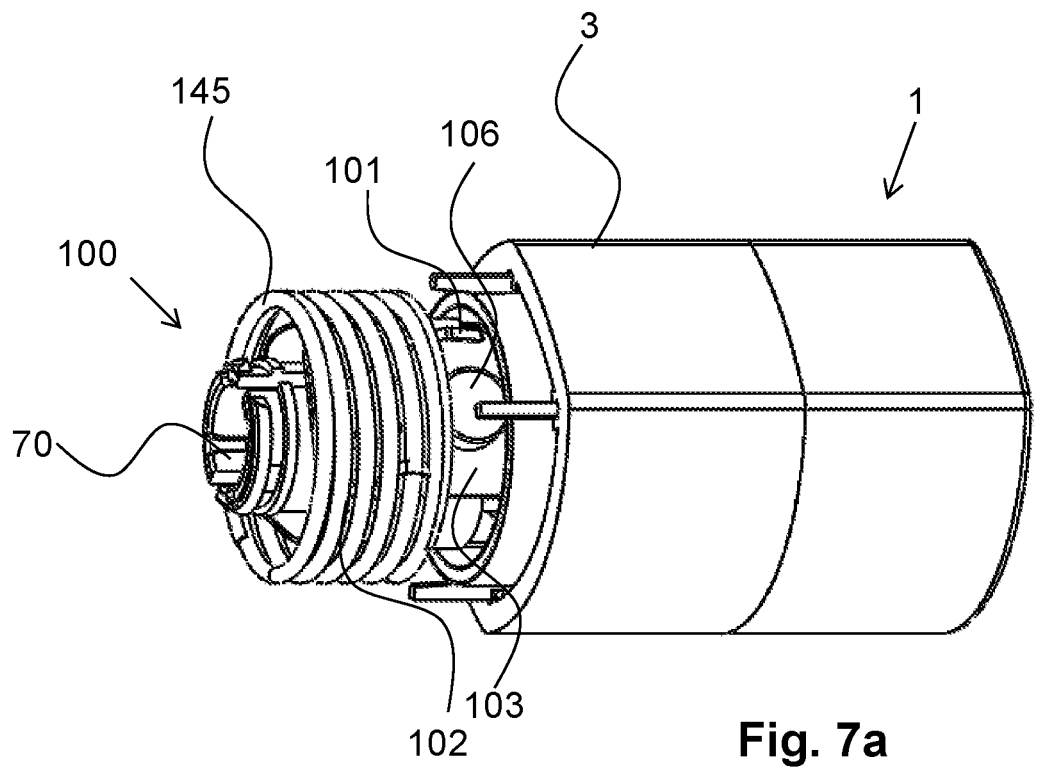
FIGS. 7a-b show parts of a medicament delivery device and of a communication device according to some embodiments.
Figure 7B:
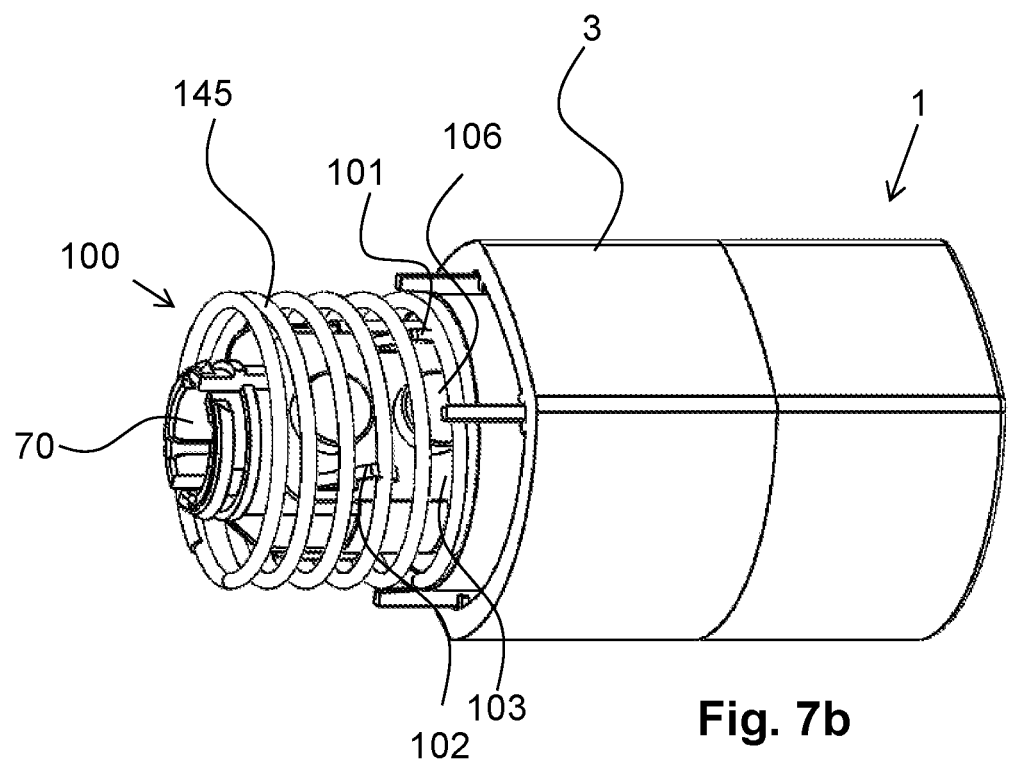

FIGS. 6a-b show sectional views of the communication device 100 being arranged/fitted within the medicament delivery device 1. FIGS. 7a-b show the communication device 100 being arranged/fitted within the medicament delivery device 1 as in FIGS. 6a-b from another view. In these figures, the communication device 100 is arranged on the plunger drive locking member 70. Thus, the PCBs 103, the first 101 and second 102 connectors, the batteries 106, the processor/transmission unit 104, and possibly also more units/arrangements described in this document, are fitted over the essentially cylindrical form of the distal end 71 and rests on the flange/stop wheel 72 at the proximal end of the plunger drive locking member 70. Thus, the communication device 100 is arranged in the internal space/volume 75 (shown in FIG. 1c) between the plunger drive locking member 70 and the container driver 32. The proximal flange/stop wheel 72 rests in the container driver 32, which initially, e.g. before penetration and/or injection, is held in place by the rotator 35. More in detail, the actuator 38 of the container driver 32 is supported by a first/higher 36 rest, and the spring 145 is in a compressed form/state, as is shown in FIGS. 6a and 7a.

When the rotator 35 is turned by the activation of the medicament delivery device 1, e.g. when medicament delivery device is pressed against the skin in order to perform the penetration, the support by the first rest 36 is rotated away from the actuator 38. The actuator 38, and thus also the container driver 32 is then moved in the proximal direction by the force of the spring 145 is performed until the actuator is supported by the second rest 37, as is illustrated in FIG. 6b. Thus, by the rotation of the rotator 35, the spring 145 is allowed to expand, whereby a translation, i.e. an axial/longitudinal movement, of a number of parts occur in relation to the flange/stop wheel and thus in relation to the communication device 100, as is also illustrated in FIG. 7b. This translation can be detected by the translation detection unit, by use of the first 101 and second 102 connectors creating initially an open circuit, as illustrated in FIGS. 6a and 7a, and then a closed circuit with the spring 145, as illustrated in FIGS. 6b and 7b. The detected translation can then be used for detection of a change of state for the medicament delivery device. Before the expansion of the spring 145, as shown FIGS. 6a and 7a, at least one of the connectors, here the first connector 101, is in contact with the non-conducting container driver 32, or is isolated in air, instead of being in contact with the spring 145, such that the open circuit is created. After the expansion of the spring 145, as shown FIGS. 6b and 7b, both of the first 101 and second 102 connectors are in electrical contact with the spring 145, whereby the closed circuit is created.

Figure 10A:
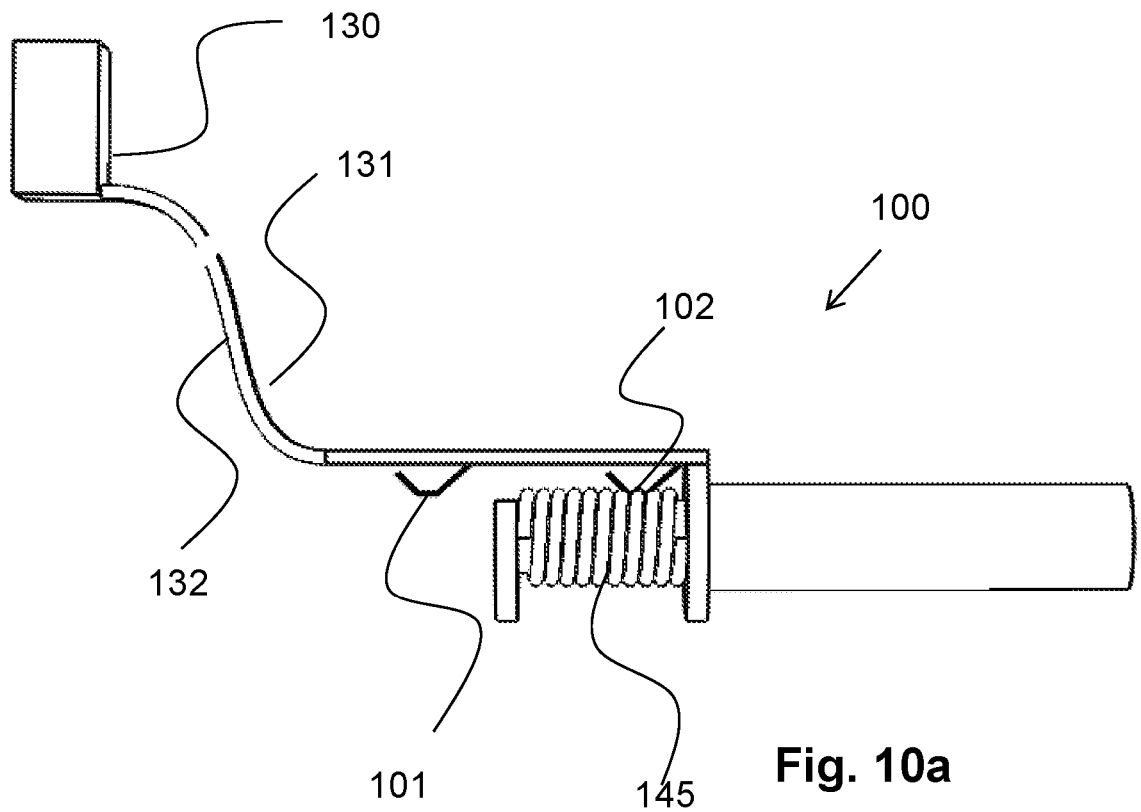
Figure 10B:
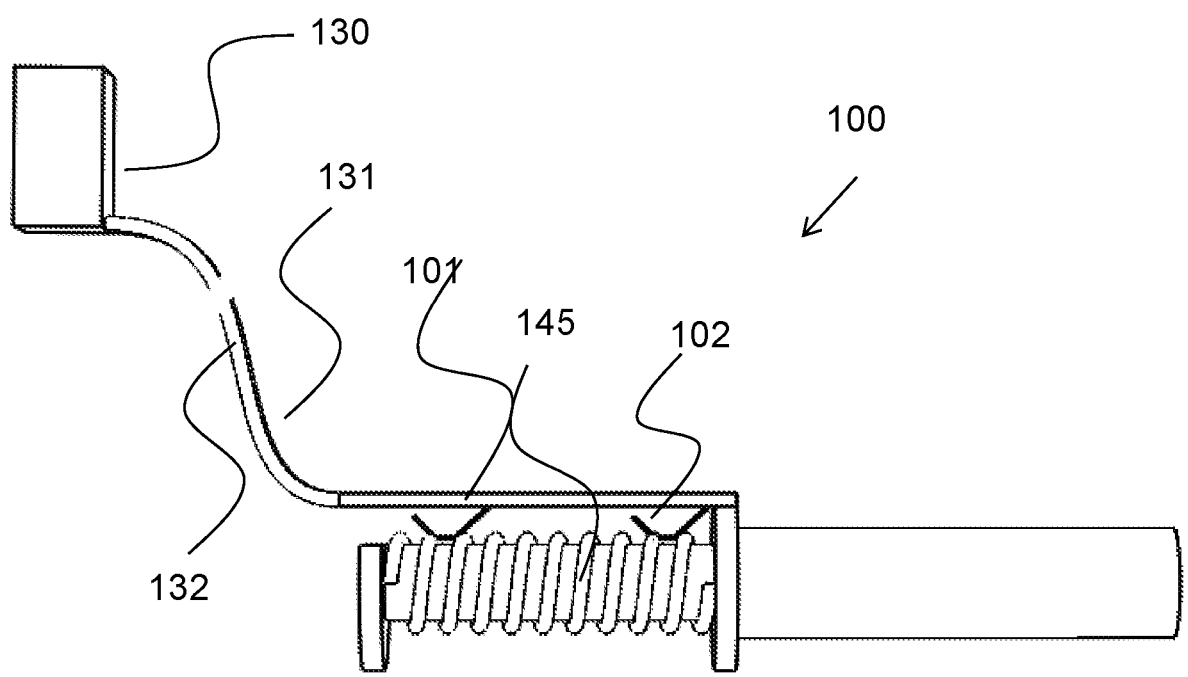
Figure 11:
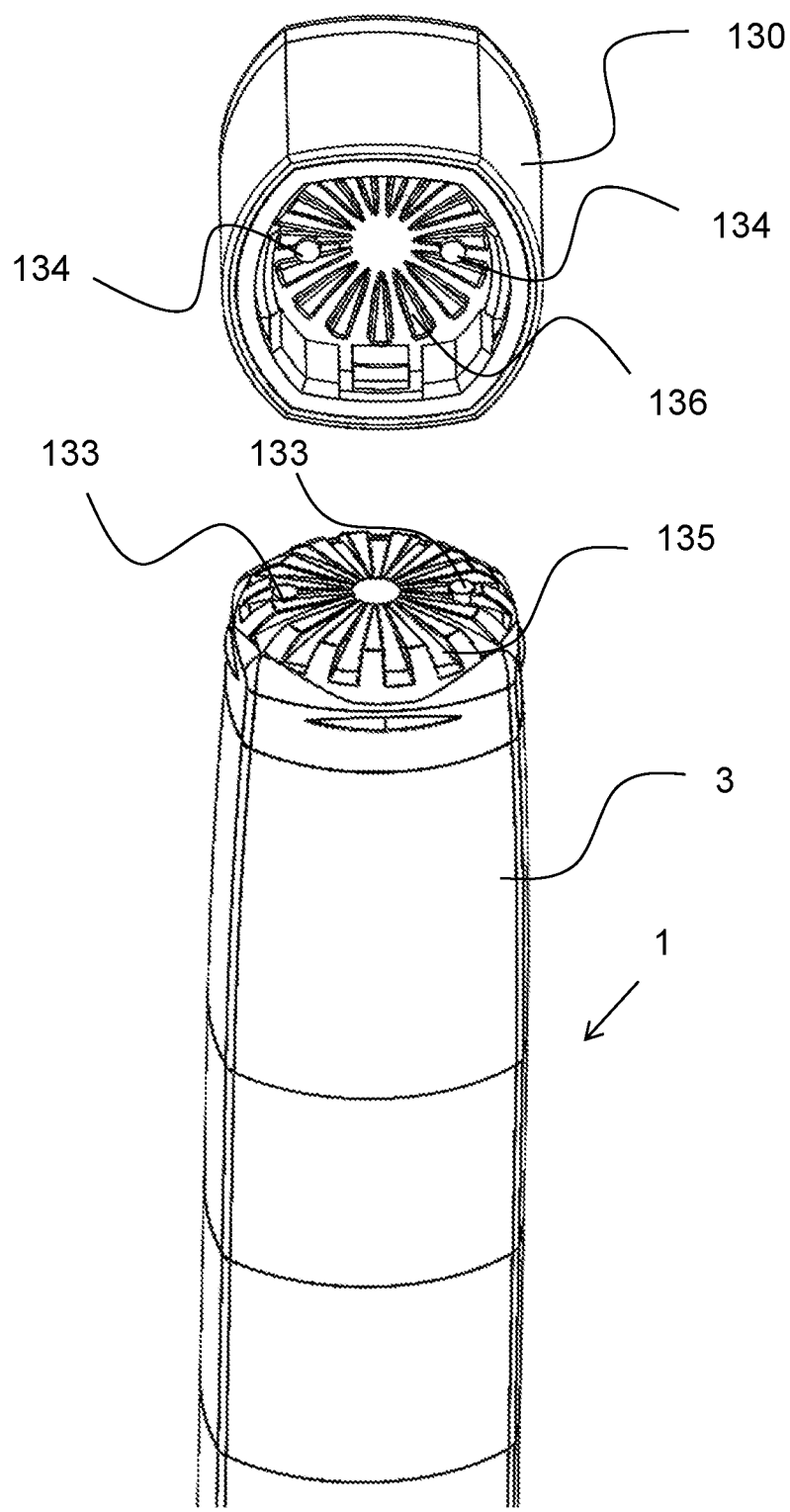
FIG. 11 schematically shows an external communication device according to some embodiments.

According to an embodiment of the present disclosure, schematically illustrated in FIGS. 10a-b and FIG. 11, the communication device 100 is included in an external unit 130 being releasably attachable to the medicament delivery device 1. For the external unit 130, the first connector 101 and the second connector 102 are coupled to the external unit 130 by a first conductor 131 and a second conductor 132, respectively. The first conductor 131 and the second conductor 132 may be provided with contact members 134 arranged on the surface of the external unit and contact members 133 arranged on the surface of the medicament delivery device. Hereby, a first 131 and second 132 conductor are provided from the external unit 130 to the first 101 and second 102 connector. The first 131 and second 132 conductors and/or the contact members 133, 134 may be applied e.g. by use of laser direct structuring (LDS), printed electronics, glued conductors, or any other suitable method for applying electrical conductors and members. The external unit may possibly include a lid, a housing and/or a cover, and is releasably attachable to the medicament delivery device 1. Essentially any releasable attachment to the medicament delivery device providing a solid attachment can here be used, such as e.g. flexible snap fits being included in the housing.

According to an embodiment, the housing can be mechanically keyed to a specific medicament delivery device. The housing may then be provided with a specific surface 136, including e.g. recesses/cavities/notches corresponding to a surface pattern 135, e.g. including protrusions, such as bars of a specific width and/or form, of a medicament delivery device 1. Thus, the communication device 100 can here only be attached to the medicament delivery device 1 if the surface pattern 136 of the housing of the external unit 130 fits into the surface pattern 135 of the specific medicament delivery device 1. Hereby, each communication device 100 may be mechanically keyed to a specific medicament delivery device 1. Also, since the two surface patterns then fit together when the communication device 100 is attached to the medicament delivery device, a more solid attachment is achieved.

According to an embodiment, the external communication device 100 includes an attachment switch, which is configured to be activated when the communication device is releasably attached to the medicament delivery device. Thus, the attachment switch is activated when the communication device 100 is mounted on the medicament delivery device 1, e.g. by mounting it on the distal end of the medicament delivery device 1 by pressing it against the distal end, thereby enabling activation of the communication device 100. Hereby, one or more parts of the communication device 100, such as e.g. the at least one translation detection arrangement, the at least one change of state detection unit, the at least one determination unit, the at least one indication unit and/or the at least one transmission unit, may be activated after the attachment switch has been activated.

The communication device 100 according to the embodiments of the present disclosure, as described herein, can be used for detecting essentially any translation for a part of the medicament delivery device. Thus, essentially any spring included in the medicament delivery device 1, which is involved in, or causes, such a translation/axial movement can be used in the open/closed circuits together with the first 101 and second 102 connectors. For example, the at least one spring can include a delivery spring configured to cause an administration of a medicament.

The at least one spring can also include a trigger button spring being configured to urge or bias the trigger button to a wanted position preferably urging the button in a distal direction.

The at least one spring can also include a compression spring as the one described above.

In case when the medicament delivery device is an injector, the at least one spring can also include a penetration spring 45, 145 being configured to move a medicament container 12 and its needle 13 towards a proximal end of the medicament delivery device 1. The at least one spring can also include a retraction spring configured to move a medicament container 12 and its needle 13 distally from a proximal end of the medicament delivery device 1 after completed injection. The at least one spring can also include a needle guard spring being configured to urge or bias a needle guard sleeve 17 towards a proximal end of the medicament delivery device 1.

The at least one spring 45, 145 can, according to an embodiment be arranged as at least one combined spring providing functions corresponding to two or more springs 45, 145, e.g. a combined penetration and injection spring. The at least one spring 45, 145 can also, according to an embodiment be arranged as separate springs, each providing a function corresponding to one of the at least one spring 45, 145, e.g. a penetration spring and a separate injection spring.

Figure 8A:
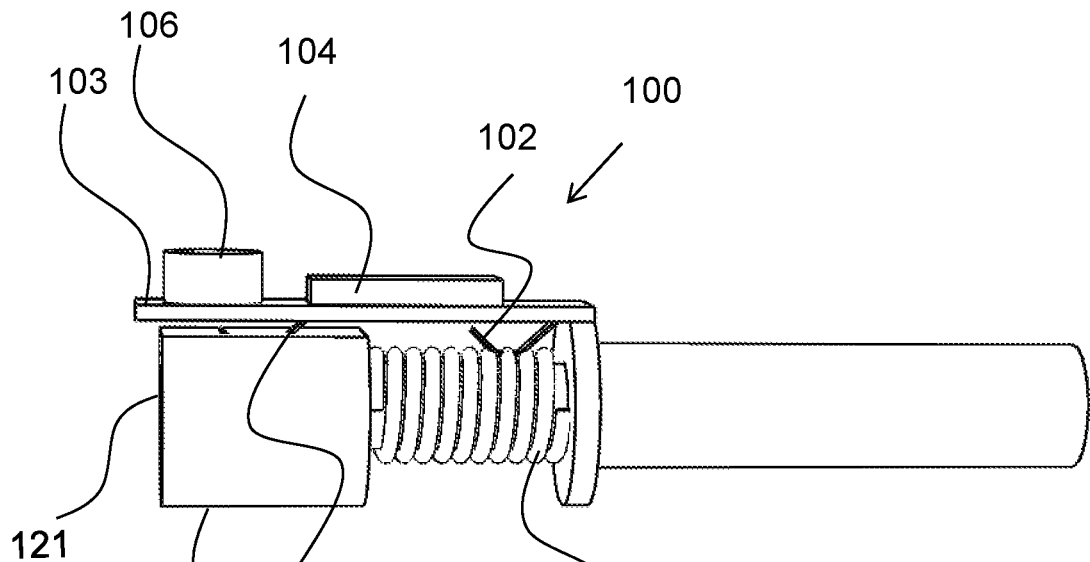
FIGS. 8a-b schematically show a spring and a communication device according to some embodiments, FIGS. 9a-b schematically show a spring and a communication device according to some embodiments, FIGS. 10a-b schematically show a spring and a communication device according to some embodiments.
Figure 8B:
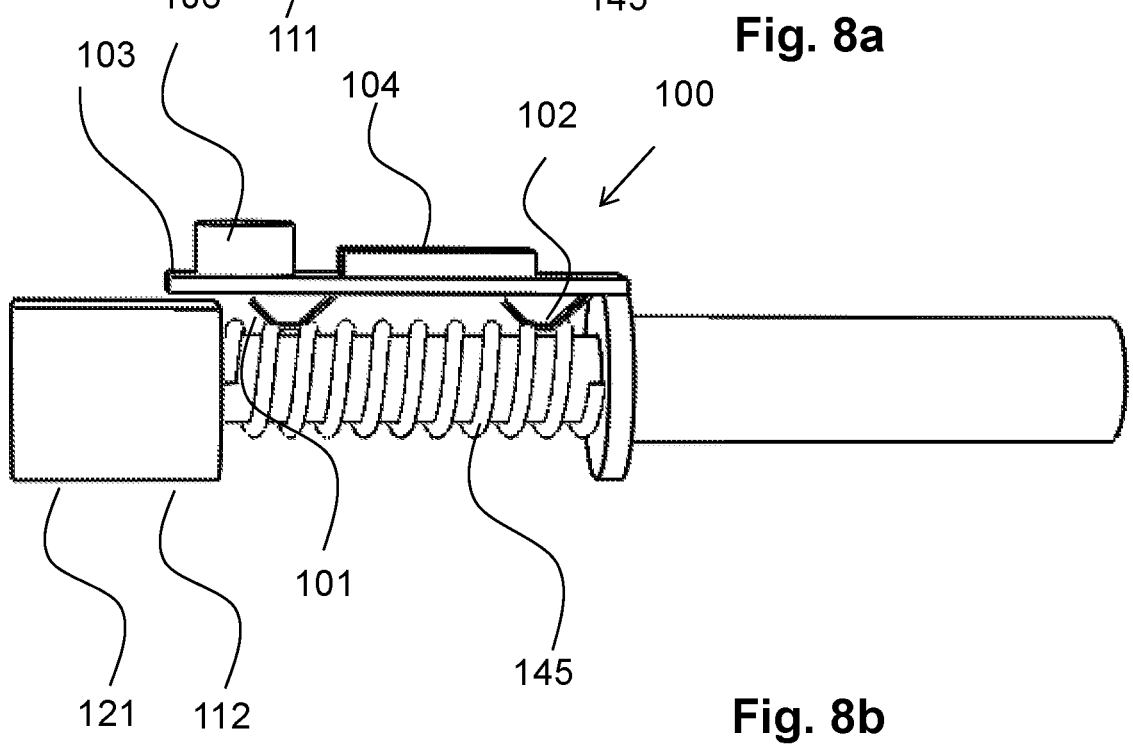

As is shown schematically in FIGS. 8a-b, at least one electrically insulating part 121 of the medicament delivery device 1 can initially, i.e. in a first state, be positioned between the spring 145 and at least one of the first connector 101 and the second connector 102. Otherwise, the communication device illustrated in FIGS. 8a-b functions as described above for FIGS. 2a-b. Thus, the first connector 101 is, by the electrically insulating part 121, insulated from electrical contact with the spring 145 when it is in a compressed form 111 in a first state for the medicament delivery device. Then, both of the first connector 101 and the second connector 102 are in electrical contact with the electrically conducting spring 145 when the spring 145 is in an expanded form 112 in a second state for the medicament delivery device. Thus, the communication device 100 according to the present disclosure uses an opening or closing of a circuit including the spring 145 in combination with its first connector 101 and its second connector 102, in order to achieve a function of a translation switch being activated by a translational movement of at least one physical part of the medicament delivery device 1.

Figure 9A:
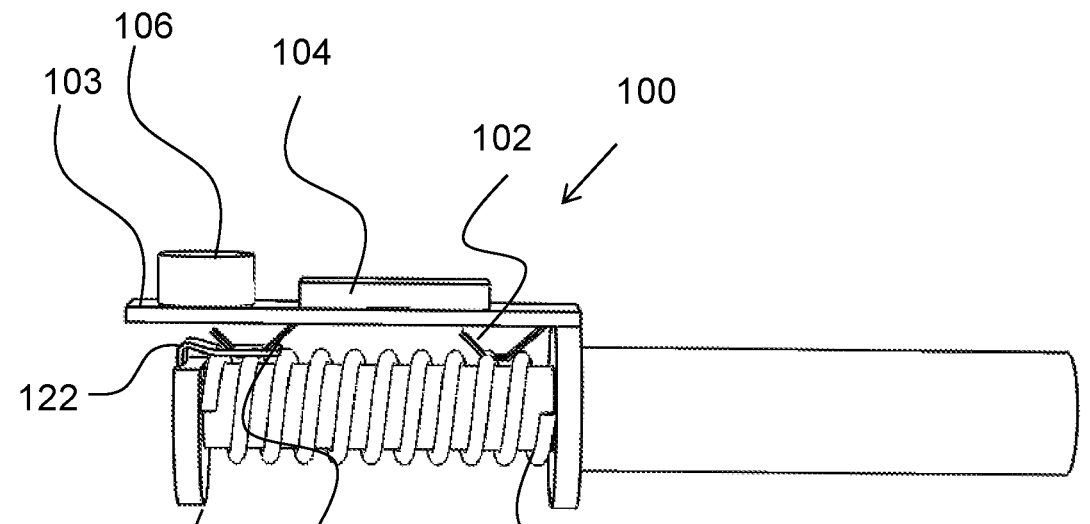
Figure 9B:
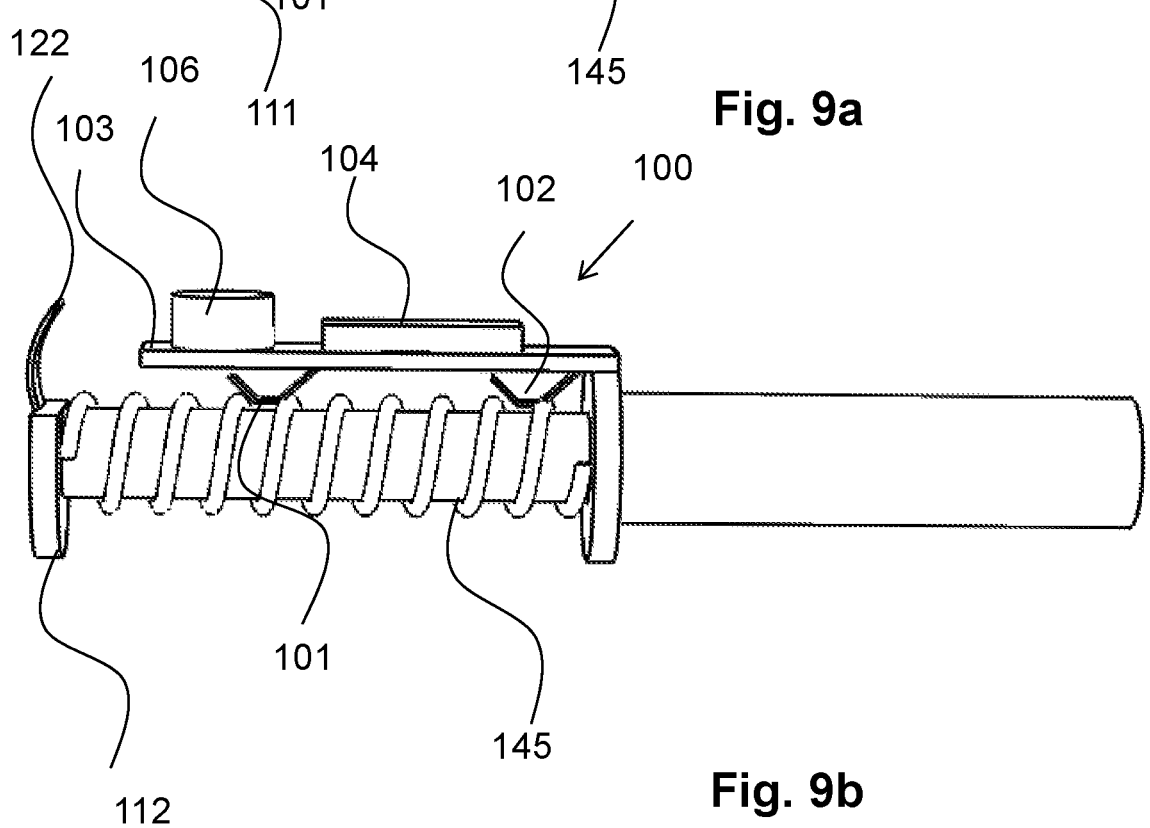

As is shown schematically in FIGS. 9a-b, at least one insulating strip 122 can initially, i.e. in a first state, be positioned between the spring 145 and at least one of the first connector 101 and the second connector 102. The at least one insulating strip 122 can here be attached to one physical part performing a translation/axial movement. Otherwise, the communication device illustrated in FIGS. 9a-b functions as described above for FIGS. 2a-b. Thus, the first connector 101 is, by the at least one electrically insulating strip 122, insulated from electrical contact with the spring 145 when it is in a compressed form 111 in a first state for the medicament delivery device. Then, both of the first connector 101 and the second connector 102 are in electrical contact with the electrically conducting spring 145 when the spring 145 is in an expanded form 112 in a second state for the medicament delivery device, since the at least one strip 122 being attached to a moving part of the device is then removed/pulled away from the connector by the expansion of the spring 145. Thus, the communication device 100 according to the present disclosure uses an opening or closing of a circuit including the spring 145 in combination with its first connector 101 and its second connector 102, in order to achieve a function of a translation switch being activated by a translational movement of at least one physical part of the medicament delivery device 1.

According to some embodiments of the present disclosure, the communication device 100 includes at least one indication unit configured to provide at least one indication of that the medicament delivery is performed. The at least one indication can include visual, audible and/or tactile indications.

An indication unit creating a visual indication can include at least one light source, such as a Light Emitting Diode (LED) is included in the indication unit. After activation of the at least one change of state detection unit, the at least one LED lights up. This light is visible for a user through a housing and/or lid, which may be semi-transparent or transparent, and/or can include a light guide, and can be used as a distinct indication for that the medicament delivery is in progress.

According to an embodiment of the present disclosure, the at least one indication being provided during the medicament delivery, e.g. the above described visual, audible and/or tactile indications, can also be provided during a predetermined time period after the delivery has ended. This is possible since the communication device according to the present disclosure is provided with a source of energy, such as a battery 106, which can be used for providing this indication, e.g. letting a LED shine, also after the medicament has been delivered. When the medicament delivery device 1 is pressed against the skin of the patient both during the delivery time, i.e. during the medicament delivery, and also during the predetermined time period after the delivery, the medicament being delivered by the medicament delivery device 1 has enough time to be absorbed by the tissue of the patient. Thus, the predetermined time period can here be set, e.g. depending on the type of drug being delivered, such that the drug is sufficiently absorbed during the rotation/delivery and the predetermined time period.

The present disclosure is not limited to the above described embodiments. Instead, the present disclosure relates to, and encompasses all different embodiments being included within the scope of the independent claims.

The invention claimed is:

1. A communication device that transmits information from a medicament delivery device, the communication device comprising:
 a mounting surface;
 a first connector coupled to the mounting surface, wherein the first connector is insulated from electrical contact with a spring of the medicament delivery device when the spring is in a compressed form, and wherein the first connector is in electrical contact with the spring of the medicament delivery device when the spring is in an expanded form;
 a second connector coupled to the mounting surface, wherein the second connector is in electrical contact with the spring of the medicament delivery device when the spring is in both the compressed form and the expanded form, and wherein the first connector and the second connector are in electrical contact with the spring creating a closed circuit when the spring is in the expanded form; and
 a transmission unit configured to provide a wireless transmission of information related to a detected translation of a physical part of the medicament delivery device to an external receiving device based on the electrical contact between the spring, the first connector, and the second connector.

2. The communication device of claim 1, further comprising:
 an electrically insulating part of the medicament delivery device being positioned between the spring and the first connector when the spring is in the compressed form.

3. The communication device of claim 1, wherein the spring is physically isolated from the first connector when the spring is in the compressed form.

4. The communication device of claim 1, further comprising:
 an insulating strip positioned between the spring and the first connector when the spring is in the compressed form.

5. The communication device of claim 1, wherein the mounting surface comprises a printed circuit board (PCB).

6. The communication device of claim 1, wherein the spring includes at least one of:
 an injection spring configured to cause an injection of a medicament;
 a penetration spring configured to move a medicament container and a needle attached to the medicament container towards a proximal end of the medicament delivery device;
 a retraction spring configured to move a medicament container and a needle attached to the medicament container distally from a proximal end of the medicament delivery device;
 a needle guard spring configured to urge a needle guard sleeve towards a proximal end of the medicament delivery device after an injection of a medicament; and
 a trigger button spring configured to urge a trigger button in a distal direction.

7. The communication device of claim 1, wherein the communication device further includes at least one indication unit configured to provide at least one indication that a medicament delivery is performed, the at least one indication being provided during the medicament delivery and also during a predetermined time period after the medicament delivery has ended.

8. The communication device of claim 7, wherein the at least one indication unit comprises:
 at least one light source configured to emit light as the at least one indication.

9. The communication device of claim 7, wherein the at least one indication unit comprises:
 at least one light guide configured to guide light being emitted by at least one light source as the at least one indication.

10. The communication device of claim 1, wherein the first connector and the second connector are arranged on an outside of the spring.

11. The communication device of claim 1, wherein at least one of the first connector and the second connector are arranged on an inside of the spring.

12. The communication device of claim 1, wherein the spring, in combination with the first connector and the second connector, is configured to function as a translation switch, the translation switch being activated by a translational movement of the physical part of the medicament delivery device.

13. The communication device of claim 1, wherein the communication device is integrated in a housing of the medicament delivery device.

14. The communication device of claim 1, wherein the spring comprises at least one combined spring providing functions corresponding to two or more springs.

15. The communication device of claim 1, wherein the spring comprises two or more separate springs, each providing a function corresponding to the spring.

16. The communication device of claim 1, wherein the communication device is included in an external unit being releasably attachable to the medicament delivery device.

17. The communication device of claim 16, wherein the first connector and the second connector are coupled to the external unit by a first conductor and a second conductor, respectively.

18. The communication device of claim 1, wherein the transmission unit is arranged on a first side of the mounting surface, and wherein the first connector and the second connector are arranged on a second side of the mounting surface opposite the first side.

19. The communication device of claim 1, wherein the compressed form of the spring comprises a pre-delivery state of the medicament delivery device, and wherein the expanded form of the spring comprises a post-delivery state of the medicament delivery device.

20. The communication device of claim 1, wherein the information related to the detected translation of the physical part of the medicament delivery device comprises one or more of:
 an identification number for the medicament delivery device;
 an identification number for a medicament being delivered by the medicament delivery device;
 an identification number for a patient using the medicament delivery device;
 an elapsed time since a delivery of a medicament occurred; and
 at least one detected change of state, wherein each state represents one step in a sequence of steps of a medicament delivery.

* * * * *